United States Patent
Yonce et al.

(10) Patent No.: US 8,046,062 B2
(45) Date of Patent: Oct. 25, 2011

(54) POST-SHOCK MANAGEMENT OF IMPLANTABLE CARDIAC DEVICE FEATURES

(75) Inventors: David J. Yonce, Fridley, MN (US); Scott Meyer, Lakeville, MN (US); David J. Ternes, Roseville, MN (US)

(73) Assignee: Cardiac Pacemakers, Inc., St. Paul, MN (US)

( * ) Notice: Subject to any disclaimer, the term of this patent is extended or adjusted under 35 U.S.C. 154(b) by 257 days.

(21) Appl. No.: 12/545,643

(22) Filed: Aug. 21, 2009

(65) Prior Publication Data

US 2009/0312810 A1 Dec. 17, 2009

Related U.S. Application Data

(62) Division of application No. 11/157,244, filed on Jun. 21, 2005, now Pat. No. 7,593,771.

(51) Int. Cl.
*A61N 1/00* (2006.01)
(52) U.S. Cl. .................. 607/4; 607/5; 607/28
(58) Field of Classification Search ............ 600/510; 607/4, 5, 27–28
See application file for complete search history.

(56) References Cited

U.S. PATENT DOCUMENTS

| | | | |
|---|---|---|---|
| 5,350,401 A | 9/1994 | Levine | |
| 5,350,410 A | 9/1994 | Kleks et al. | |
| 5,797,967 A | 8/1998 | KenKnight | |
| 6,157,859 A | 12/2000 | Alt | |
| 6,490,486 B1 | 12/2002 | Bradley | |
| 6,654,639 B1 | 11/2003 | Lu | |
| 6,708,058 B2 | 3/2004 | Kim et al. | |
| 6,738,669 B1 | 5/2004 | Sloman et al. | |
| 6,788,971 B1 | 9/2004 | Sloman et al. | |
| 2003/0050671 A1 | 3/2003 | Bradley | |
| 2003/0083710 A1 | 5/2003 | Ternes et al. | |
| 2003/0083711 A1 | 5/2003 | Yonce et al. | |
| 2004/0082975 A1 | 4/2004 | Meyer et al. | |
| 2004/0127950 A1 | 7/2004 | Kim et al. | |
| 2004/0243014 A1 | 12/2004 | Lee et al. | |

OTHER PUBLICATIONS

Notice of Allowance dated Apr. 30, 2009 from U.S. Appl. No. 11/157,544, 4 pages.
Office Action Response dated Jan. 9, 2009 from U.S. Appl. No. 11/154,544, 8 pages.
Office Action Response dated Jun. 6, 2008 from U.S. Appl. No. 11/154,544, 7 pages.
Office Action dated May 1, 2008 from U.S. Appl. No. 11/154,544, 9 pages.
Office Action dated Sep. 9, 2008 from priority U.S. Appl. No. 11/157,244.

*Primary Examiner* — Mark W Bockelman
(74) *Attorney, Agent, or Firm* — Hollingsworth & Funk, LLC

(57) ABSTRACT

Systems and methods of managing features or functions of an implantable cardiac device involve forming a baseline evoked response template prior to delivery of defibrillation therapy to a patient's heart, and acquiring a post-shock evoked response signal subsequent to defibrillation therapy delivery. The baseline evoked response template is compared to the post-shock evoked response signal. A determination is made whether to enable, disable or adjust a cardiac device feature based on the comparison. The cardiac device feature may be a therapy feature, a monitoring feature, or a diagnostic feature.

20 Claims, 6 Drawing Sheets

POST-SHOCK MANAGEMENT OF IMPLANTABLE CARDIAC DEVICE FEATURES

RELATED APPLICATIONS

This application is a division of U.S. patent application Ser. No. 11/157,244 filed on Jun. 21, 2005, to which Applicant claims priority under 35 U.S.C. §120, and which is incorporated herein by reference.

FIELD OF THE INVENTION

The present invention relates generally to implantable medical devices, and more particularly to managing automatic capture verification using baseline evoked response template and post-shock evoked response signal matching.

BACKGROUND OF THE INVENTION

The healthy heart produces regular, synchronized contractions. Rhythmic contractions of the heart are normally initiated by the sinoatrial (SA) node, which is a group of specialized cells located in the upper right atrium. The SA node is the normal pacemaker of the heart, typically initiating 60-100 heartbeats per minute. When the SA node is pacing the heart normally, the heart is said to be in normal sinus rhythm.

If the heart's electrical activity becomes uncoordinated or irregular, the heart is denoted to be arrhythmic. Cardiac arrhythmia impairs cardiac efficiency and may be a potential life-threatening event. Cardiac arrhythmias have a number of etiological sources, including tissue damage due to myocardial infarction, infection, or degradation of the heart's ability to generate or synchronize the electrical impulses that coordinate contractions.

Bradycardia occurs when the heart rhythm is too slow. This condition may be caused, for example, by impaired function of the SA node, denoted sick sinus syndrome, or by delayed propagation or blockage of the electrical impulse between the atria and ventricles. Bradycardia produces a heart rate that is too slow to maintain adequate circulation.

When the heart rate is too rapid, the condition is denoted tachycardia. Tachycardia may have its origin in either the atria or the ventricles. Tachycardias occurring in the atria of the heart, for example, include atrial fibrillation and atrial flutter. Both conditions are characterized by rapid contractions of the atria. Besides being hemodynamically inefficient, the rapid contractions of the atria may also adversely affect the ventricular rate.

Ventricular tachycardia occurs, for example, when electrical activity arises in the ventricular myocardium at a rate more rapid than the normal sinus rhythm. Ventricular tachycardia may quickly degenerate into ventricular fibrillation. Ventricular fibrillation is a condition denoted by extremely rapid, uncoordinated electrical activity within the ventricular tissue. The rapid and erratic excitation of the ventricular tissue prevents synchronized contractions and impairs the heart's ability to effectively pump blood to the body, which is a fatal condition unless the heart is returned to sinus rhythm within a few minutes.

Implantable cardiac rhythm management systems have been used as an effective treatment for patients with serious arrhythmias, as well as for patients with conditions such as heart failure. These systems typically include one or more leads and circuitry to sense signals from one or more interior and/or exterior surfaces of the heart. Such systems also include circuitry for generating electrical pulses that are applied to cardiac tissue at one or more interior and/or exterior surfaces of the heart. For example, leads extending into the patient's heart are connected to electrodes that contact the myocardium for sensing the heart's electrical signals and for delivering pulses to the heart in accordance with various therapies for treating arrhythmias.

Typical implantable cardioverter/defibrillators (ICDs) include one or more endocardial leads to which at least one defibrillation electrode is connected. Such implantable cardioverter/defibrillators are capable of delivering high-energy shocks to the heart, interrupting the ventricular tachyarrhythmia or ventricular fibrillation, and allowing the heart to resume normal sinus rhythm. Implantable cardioverter/defibrillators may also include pacing functionality.

SUMMARY OF THE INVENTION

The present invention is broadly directed to management of implantable cardiac device features following delivery of high voltage therapy to a patient's heart. Aspects of the invention are directed to determining a patient's cardiac condition before and after delivery of a high voltage cardiac therapy, such as tachyarrhythmia therapy. Further aspects of the present invention are directed to determining a duration of time required for cardiac tissue to recover from delivery of a high voltage therapy to a state reasonably approximating a pre-therapy delivery state. Based on the duration of this recovery time, features and/or functions of an implantable cardiac device may be initiated, terminated or otherwise altered.

Implantable cardiac device features that may be initiated, terminated or altered based on a determined post-shock cardiac tissue recovery time may include a therapy feature, a monitoring feature or a diagnostic feature, for example. Such features may include, for example, enabling or disabling an automatic capture verification or autothreshold testing feature, or modifying one or more parameters associated with automatic capture verification or autothreshold testing. Such features may also include reverting from use of post-shock bradycardia pacing parameters to use of normal bradycardia pacing parameters. Still other features may include enabling autonomic balance monitoring after determining a patient's post-shock cardiac tissue recovery time.

According to one embodiment, a method for managing features of an implantable cardiac device involves forming a baseline evoked response template prior to delivery of defibrillation therapy to a patient's heart, and acquiring a post-shock evoked response signal subsequent to defibrillation therapy delivery. The baseline evoked response template is compared to the post-shock evoked response signal. A determination is made whether to enable, disable or adjust a cardiac device feature based on the comparison. The cardiac device feature may be a therapy feature, a monitoring feature, or a diagnostic feature, for example.

In a further embodiment, a method for managing capture testing in an implantable cardiac device, for example, involves forming a baseline evoked response template prior to delivery of defibrillation therapy to a patient's heart, acquiring a post-shock evoked response signal subsequent to defibrillation therapy delivery, and comparing the baseline evoked response template and post-shock evoked response signal. A determination is made whether to enable, disable or adjust capture testing based on the comparison. The capture testing may involve automatic capture verification testing. The capture testing may also involve autothreshold testing.

According to another embodiment, a cardiac rhythm management system includes one or more electrodes configured to electrically couple to a heart and a pulse generator coupled to the one or more electrodes. The pulse generator is configured to deliver electrical therapy to the heart. The system further includes a sensing system coupled to the one or more electrodes and configured to sense a cardiac signal associated with delivery of electrical therapy to the heart using the one or more cardiac electrodes. The system also includes circuitry configured to manage various features of the cardiac rhythm management system. The circuitry is configured to acquire a post-shock evoked response signal subsequent to defibrillation therapy delivery using signals received from the sensing system and compare a baseline evoked response template and the post-shock evoked response signal. The circuitry is further configured to enable, disable or adjust a feature of the cardiac rhythm management system based on the comparison.

In accordance with a further embodiment, a cardiac rhythm management system includes one or more electrodes configured to electrically couple to a heart and a pulse generator coupled to the one or more electrodes. The pulse generator is configured to deliver electrical therapy to the heart. The system further includes a sensing system coupled to the one or more electrodes and configured to sense a cardiac signal associated with delivery of electrical therapy to the heart using the one or more cardiac electrodes. The system also includes circuitry configured to manage capture testing. The circuitry is configured to acquire a post-shock evoked response signal subsequent to defibrillation therapy delivery using signals received from the sensing system, compare a baseline evoked response template and the post-shock evoked response signal, and determine whether to enable or disable capture testing based on the comparison. The circuitry may be configured to perform automatic capture verification testing and may further be configured to perform autothreshold testing.

The above summary of the present invention is not intended to describe each embodiment or every implementation of the present invention. Advantages and attainments, together with a more complete understanding of the invention, will become apparent and appreciated by referring to the following detailed description and claims taken in conjunction with the accompanying drawings.

Figure 1:
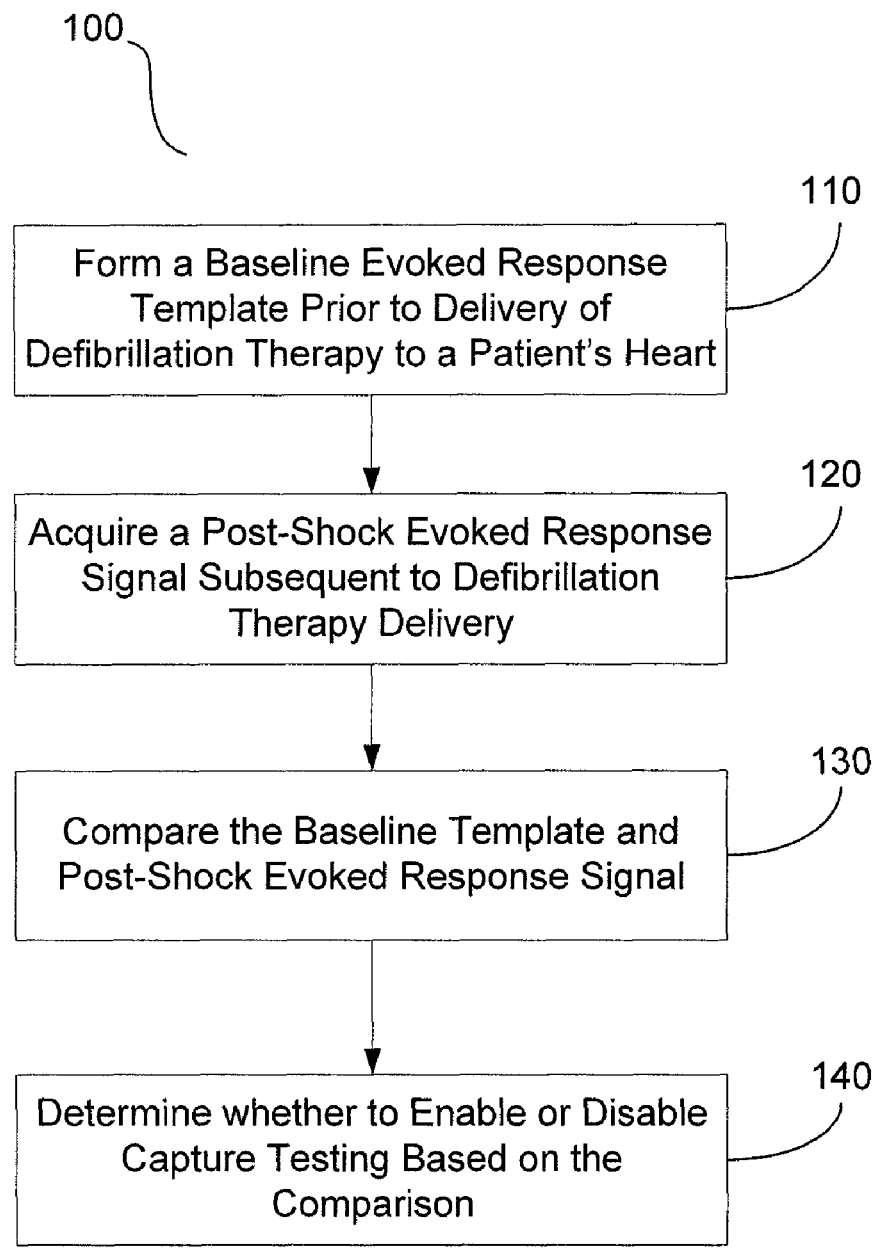
FIG. 1 is a flowchart of a method for managing capture testing in accordance with embodiments of the invention.

While the invention is amenable to various modifications and alternative forms, specifics thereof have been shown by way of example in the drawings and will be described in detail below. It is to be understood, however, that the intention is not to limit the invention to the particular embodiments described. On the contrary, the invention is intended to cover all modifications, equivalents, and alternatives falling within the scope of the invention as defined by the appended claims.

DETAILED DESCRIPTION OF VARIOUS EMBODIMENTS

In the following description of the illustrated embodiments, references are made to the accompanying drawings that form a part hereof, and in which are shown by way of illustration, various embodiments by which the invention may be practiced. It is to be understood that other embodiments may be utilized, and structural and functional changes may be made without departing from the scope of the present invention.

Pacing a patient's heart with an ICD produces an evoked response which has been shown to be highly consistent in terms of amplitude and morphology, even when the pacing voltage is varied during normal pacing therapy. Thus, under normal conditions, where paced morphology is stable, template-based capture testing systems can be used to determine and identify a loss of capture.

However, following a high energy shock delivered from an ICD to a patient's heart, the morphology may change considerably because of a stunned myocardium. This may produce an erroneous response from a template-based capture testing system.

Disabling capture testing for a predetermined length of time following a high voltage defibrillation is one method used to manage morphology changes due to a stunned myocardium. However, the predetermined length of time could potentially be too long, for instance, if no stunning of the myocardium occurs.

The present invention involves methods for managing implantable cardiac device features, such as capture testing, based on a patient's cardiac condition before and after delivery of high voltage therapy to the patient's heart. For example, methods for disabling capture testing while performing additional processing to assess the stability of the post-shock signal are described. Assessing post-shock signals may allow for management of a capture testing mode according to a post-shock recovery time following a high voltage defibrillation without losing bradycardia therapy, for example. The present invention also involves monitoring post-shock cardiac activity which may be used to determine when a patient's cardiac state is reasonably close to a pre-shock state. This may allow cardiac device features, such as a capture testing mode, to be enabled, disabled or adjusted based on a determination of when cardiac conditions match a pre-shock state. Capture testing, in accordance with embodiments of the invention, may include one or both of automatic capture verification and autothreshold testing.

The present invention focuses on a patient's cardiac condition before and after delivery of tachyarrhythmia therapy in order to determine whether to enable, disable or adjust capture testing. Tachyarrhythmia therapy is delivered to the heart during a period of suspended capture testing. Enabling a capture testing mode is delayed for at least a post-shock delay period. The post-shock delay period may be a predetermined period of time prior to analyzing a first post-shock signal. Capture testing may be delayed beyond the predetermined post-shock delay period based on the state of the myocardium. As will be described below, the delay period is dependent on whether the post-shock signal and pre-shock evoked response templates match.

Embodiments of the present invention may be applied to a variety of cardiac detection and therapy processes without substantial modification to such processes, e.g., one and twochannel morphology-based rhythm analyses may determine the presence of tachycardia and may be used in combination with embodiments of the present invention. Various techniques for detecting capture and/or other cardiac responses to pacing, aspects of which may be utilized in capture testing management according to embodiments of the present invention, are described in commonly assigned U.S. patent application Ser. No. 10/335,599 filed on Dec. 31, 2002; and U.S. patent application Ser. No. 10/733,869 filed on Dec. 11, 2003, which are hereby incorporated herein by reference.

Referring to FIG. 1, there is shown a flowchart of a method for managing capture testing in accordance with embodiments of the invention. A baseline evoked response template is formed 110 sometime prior to delivery of defibrillation therapy to a patient's heart. A post-shock evoked response signal is acquired 120 subsequent to defibrillation therapy delivery. Baseline and post-shock evoked response templates are compared 130. A determination 140 is made, based on the comparison, as to whether to enable or disable capture testing. The determination 140 may further include determining whether to adjust capture testing.

In a capture testing mode, an evoked response is sensed and a baseline evoked response template is acquired. A capture testing mode may include one or both of an automatic capture verification mode and autothreshold mode. Evoked responses are typically sensed on a beat by beat basis in automatic capture verification mode. Autothreshold tests provide for the detection of a patient's capture threshold using primary step-down pace pulses, such tests typically being implemented on a scheduled basis. Autothreshold tests allow the cardiac rhythm management system to adjust the energy level of pace pulses to correspond to the optimum energy expenditure that reliably produces a contraction.

Baseline evoked response templates change according to a variety of patient conditions. Such conditions may include cardiac changes described below, or may include patient condition changes, such as patient activity, patient wakefulness, or patient sleep inducing a change in an evoked response template. Acquiring a representative baseline evoked response template captures a representation of current patient conditions, and allows the post-shock signal to be matched with the patient's pre-tachyarrhythmia cardiac characteristics rather than matching with obsolete or suspect cardiac measurements. Because changes in patient conditions can result in a change of a patient's baseline, a baseline evoked response template may be periodically reacquired.

One or more post-shock evoked response signals used for comparison with the evoked response template are acquired subsequent to a defibrillation therapy, which may be during a period of suspended capture testing. Post-shock evoked response signals are acquired after an adequate period of time in order for the cardiac tissue to return to a normal state. Post-shock recovery periods, which may correspond to a capture testing delay period, can range anywhere from 10 seconds to several hours. Additionally, post-shock evoked response signals can include post-shock evoked response templates.

A patient's post-shock recovery period may be determined during implantation induction testing. For example, when a patient is induced into ventricular fibrillation and then shocked into a normal sinus rhythm, the period for the heart to recover back to its pre-shock state may be determined. During implantation, electrodes are physically secured to the cardiac tissue and are acutely fixed. Measurements taken from acutely fixed electrodes during induction testing may be used to determine a period of time myocardial tissue takes to return to a pre-shock state. The time period may be used to delay acquisition of the post-shock signal once cardiac shock therapy is delivered to the heart.

Another method for determining a patient's post-shock recovery period may involve measuring the patient's post-shock recovery period after chronic lead fixation has been established. In-growth of the cardiac leads over time affixes the leads to the cardiac tissue and results in an increase in capture threshold. This is due to an increase in impedance resulting from the tissue in-growth. With the increased impedance, due to chronic fixation, the recovery period will be different than the recovery period for leads fixed acutely.

The acquired baseline evoked response template and post-shock evoked response signal are compared to determine if the signals match, which may be indicative of a stabilized state of the myocardium. Comparison methods may include using signal morphology analysis, feature correlation coefficient (FCC) or other correlation methods, e.g., point-by-point. In addition, peak-based analysis can be used in embodiments of the invention and can include analyzing the distribution of peaks, windows around peaks, or peak widths.

When a comparison of the baseline evoked response template and post-shock evoked response signal match, the myocardium has reached a point of stability and the capture testing mode is enabled allowing initiation of capture testing. When the template and signal do not match, the myocardium has not reached a stability level consistent with the level determined before delivery of defibrillation therapy. In the absence of a match between the evoked response template and post-shock evoked response signal, the suspended capture testing continues and another post-shock evoked response signal can be acquired and compared to the baseline evoked response template. While capture testing is disabled, the cycle may continue, usually for a predetermined period of time or until the template and signal match. After a predetermined period of comparison without a match, the myocardium is considered to be consistently unstable compared to the myocardium's pre-defibrillation state. Unstable myocardial tissue may be an indication that the myocardium has undergone a permanent change which may result in a baseline evoked response template change. In this instance, the capture testing mode is enabled and a new baseline evoked response template is acquired that is representative of the permanently changed myocardium.

A permanent change in myocardial tissue may result in a change in right ventricular amplitude or capture amplitude, both of which are roughly correlated to heart failure (HF), or the potential for progression to heart failure. Similarly, an increasing QRS complex width may be indicative of heart failure. When a permanent myocardial change is considered to have occurred, a physician notification signal may be sent to a patient-external device, such as an advanced patient management (APM) system.

Figure 2:
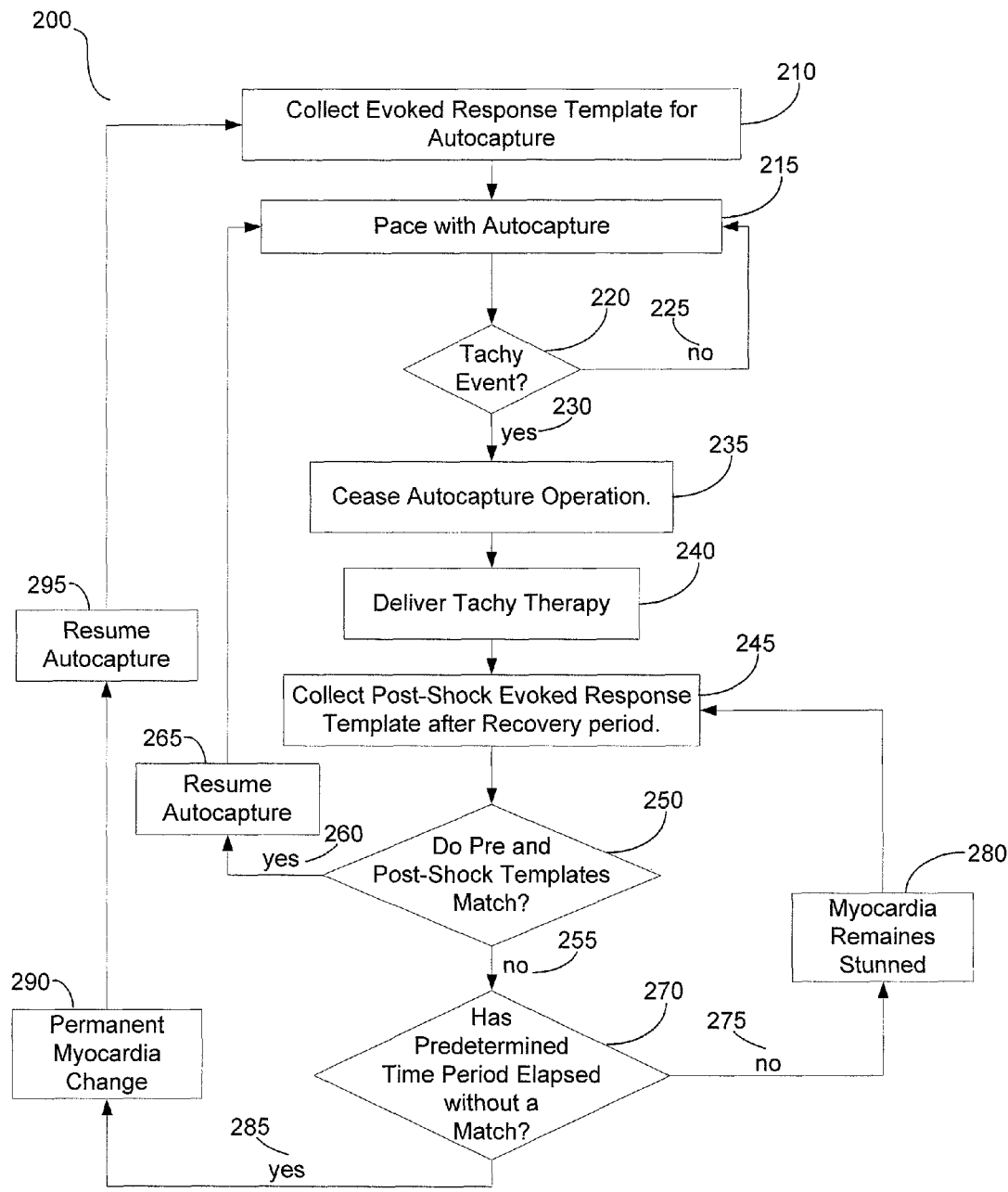
FIG. 2 is a flowchart of a method for managing capture testing in accordance with embodiments of the invention.

FIG. 2 is a flowchart of a method for managing capture testing in accordance with embodiments of the invention. A first evoked response template is collected 210 in an automatic capture verification mode. Pacing 215 with automatic capture verification is conducted and a determination 220 is made as to whether a tachycardia event has occurred. If no tachycardia event has occurred 225, pacing 215 with automatic capture verification continues.

When a tachycardia event is detected 230, automatic capture verification operations are ceased 235, and tachycardia therapy is delivered 240. Tachyarrhythmia therapy may include, for example an antitachycardia pacing (ATP) or high-voltage shock (e.g., cardioversion or defibrillation therapy). When automatic capture verification ceases, the pacing output voltages are increased to provide a safe margin against a threshold increase following the tachycardia therapy. Clinical data suggests the pacing voltage should be increased to greater than about four times the pre-shock threshold level.

Following a post-shock recovery period, which may be a predetermined or variable recovery period based on patient conditions, a post-shock evoked response template is collected 245. A determination 250 is made as to whether the first evoked response template and the post-shock evoked response template match. When the templates match 260, automatic capture verification is resumed 265.

When the templates do not match 255, a determination 270 is made as to whether a predetermined time has elapsed without a matching first and post-shock evoked response template. If the predetermined time has not elapsed 275, then the myocardium remains stunned 280.

A post-shock evoked response template is collected 245 after 30 minutes, for example, for further matching determinations 250. When the predetermined time has elapsed 285 without a match between the pre-shock and post-shock templates, a permanent change 290 in the myocardium is considered to have occurred. If a permanent change to the myocardium results, then automatic capture verification is resumed 295 and a new evoked response template is collected 210.

Figure 3:
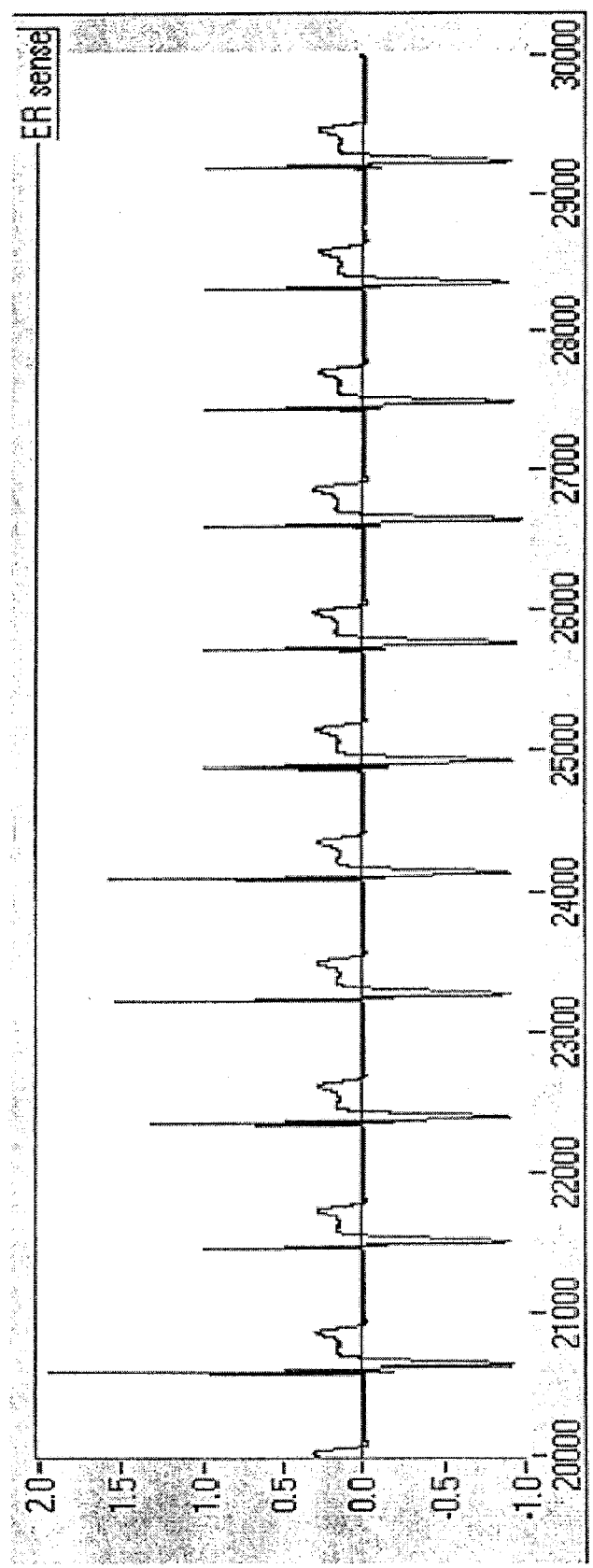
FIG. 3 is a graph illustrating a cardiac signal that indicates capture.

When pacing pulses delivered to the heart produce a depolarization wave in cardiac tissue resulting in a cardiac contraction, a captured response may be detected by examining the cardiac signal following the delivery of the pacing pulse. FIG. 3 is a graph illustrating output of a cardiac signal that consistently indicates an evoked response following a sequence of pacing pulses.

Figure 4:
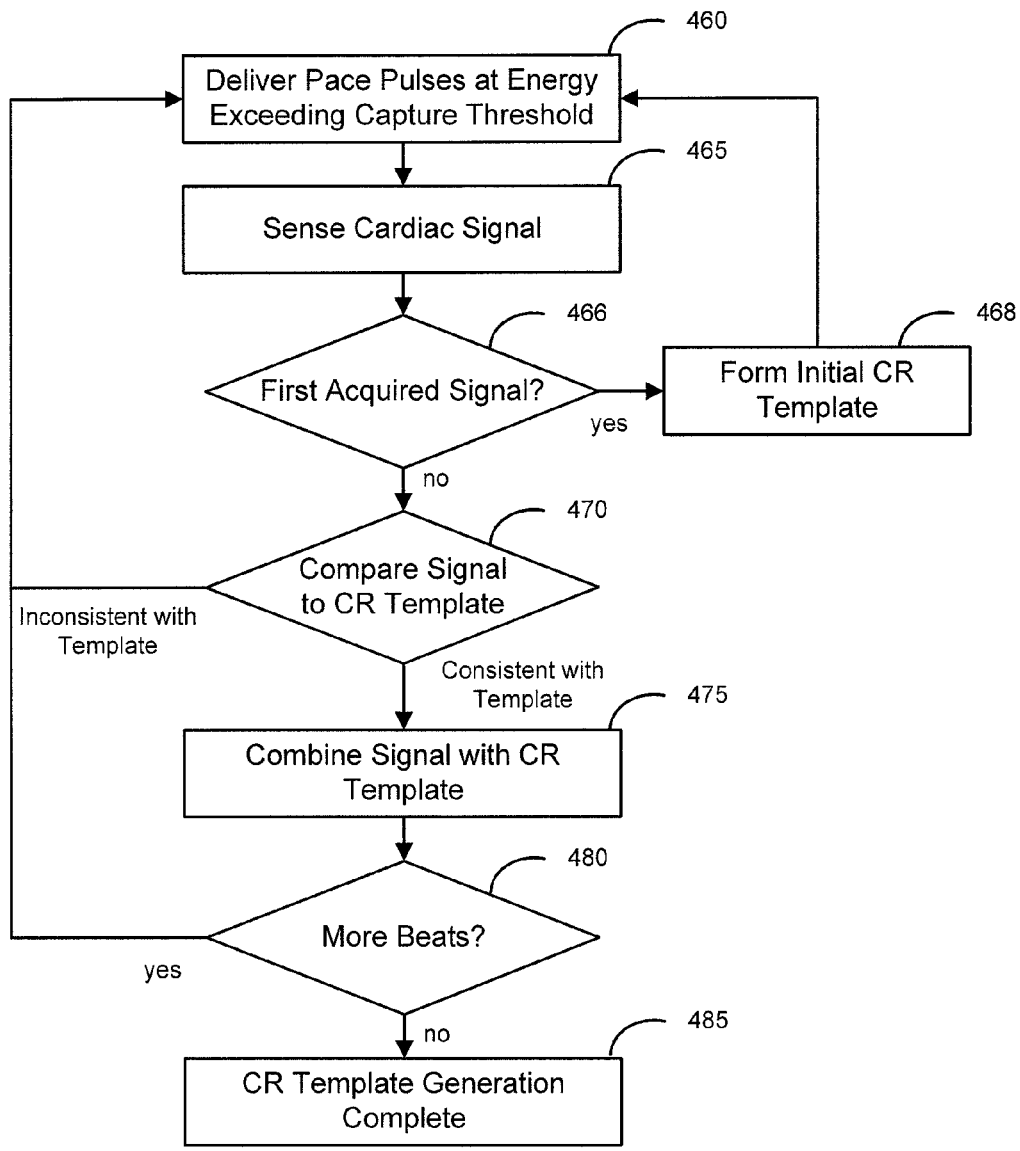
FIG. 4 is a flowchart illustrating a method of forming a captured response (CR) template in accordance with embodiments of the invention.

FIG. 4 is a flowchart illustrating a method of forming an evoked response (ER) template in accordance with embodiments of the invention. Pacing pulses are delivered 460 to a heart chamber at a pacing energy exceeding the evoked response threshold for the chamber. The cardiac signal following delivery of the pacing pulse is sensed 465. If the sensed cardiac signal is the first acquired signal 466, the cardiac signal is used 468 to form an initial ER template. If the sensed cardiac signal is not the first acquired signal 466, then the sensed cardiac signal is compared 470 to the existing ER template. If the sensed cardiac signal is consistent with 470 the ER template, then it is combined 475 with the ER template. A cardiac signal may be considered to be consistent with a template if the features, samples, or other morphological characteristics of the cardiac signal are determined to be sufficiently similar to the template features, samples, or morphological characteristics. Various techniques may be used to compare a template and a cardiac signal, including the correlation techniques described herein.

In some implementations, a cardiac signal that is consistent 470 with the ER template may be combined with the ER template by averaging the cardiac signal and the ER template sample by sample, or by other averaging methods. In other implementations, different methods of combining the cardiac signal with the template may be used. If more beats are available 480 for ER template generation then the process of blocks 460-475 is repeated. If no more beats are available for ER template generation, then the ER template generation process is complete 485.

In one implementation, the comparison between an existing ER template and a sensed cardiac signal may be accomplished by calculating a correlation coefficient (CC) comparing the sensed cardiac signal and the ER template using a technique such as Correlation Waveform Analysis (CWA). According to this technique, a correlation coefficient (CC) may be calculated to compare the sensed cardiac signal to the ER template sample by sample. Methods and systems for using correlation coefficients for ER template and cardiac signal comparison are described in commonly owned U.S. Pat. No. 7,319,900, which is hereby incorporated herein by reference.

In another implementation, features used to form an existing ER template and features of a sensed cardiac signal may be compared by calculating a feature correlation coefficient (FCC). The FCC may be determined, for example, using every fourth sample of the cardiac signal and the evoked response template. Methods and systems for using feature correlation coefficients for ER template and cardiac signal comparison are described in previously incorporated U.S. Pat. No. 7,319,900.

The ER template may be periodically updated using cardiac signals classified as evoked responses. Updating the ER template allows the ER template to adapt to slow variations in the patient's evoked response over time. Updating the ER template may be accomplished by averaging, or otherwise combining, the samples or feature points of an existing ER template with corresponding samples or feature points of cardiac signals representing evoked response beats.

If the ER template is updated, the classification windows based on ER template features or morphology may also be updated. For example, the timing of a classification window based on an ER template feature may be modified to accommodate an updated timing of the ER template feature. Further, the duration of one or more of the classification windows may be modified based on updated information with respect to the ER template morphology.

In one implementation, an ER template may be formed or updated during an autothreshold test. The test may deliver pacing pulses to the heart at an initially high pacing energy and ramp down the pacing energy over a series of pulses until a loss of capture is detected. An ER template may be formed or updated using the cardiac signals associated with capture responses following delivery of high energy pace pulses to the heart during autothreshold testing.

In another implementation, an ER template may be formed or updated in an automatic capture verification mode. While in automatic capture verification mode, capture is detected beat to beat. An ER template may be formed or updated using the cardiac signals associated with captured responses detected in automatic capture verification mode.

Figure 5:
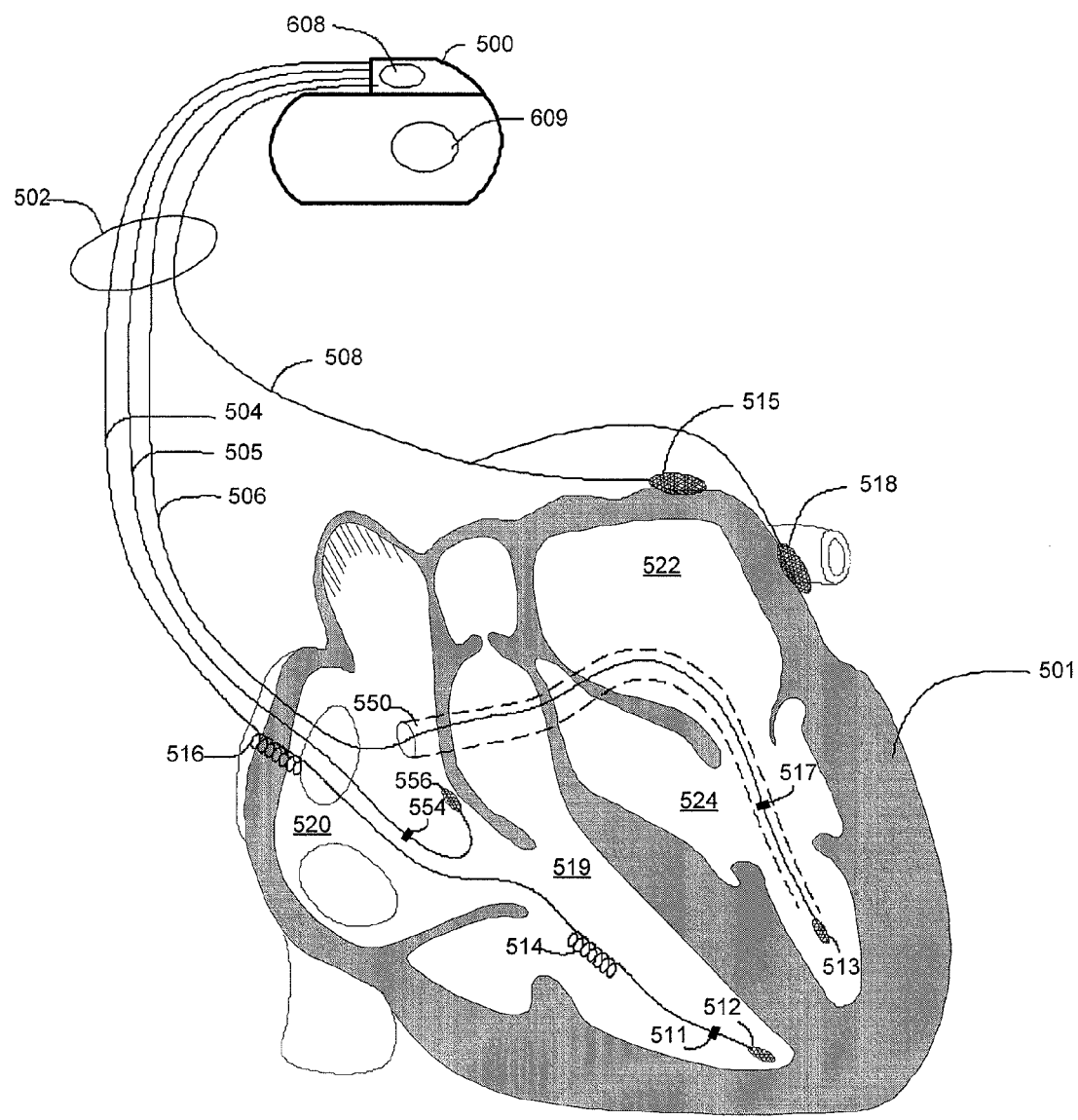
FIG. 5 is a partial view of one embodiment of an implantable medical device in accordance with embodiments of the invention.

Referring now to FIG. 5 of the drawings, there is shown a cardiac rhythm management system that may be used to implement capture testing management methods of the present invention. The cardiac rhythm management system in FIG. 5 includes an ICD 500 electrically and physically coupled to a lead system 502. The housing and/or header of the ICD 500 may incorporate one or more electrodes 608, 609 used to provide electrical stimulation energy to the heart and to sense cardiac electrical activity. The ICD 500 may utilize all or a portion of the ICD housing as a can electrode 609. The ICD 500 may include an indifferent electrode positioned, for example, on the header or the housing of the ICD 500. If the ICD 500 includes both a can electrode 609 and an indifferent electrode 608, the electrodes 608, 609 typically are electrically isolated from each other.

The lead system 502 is used to detect electric cardiac signals produced by the heart 501 and to provide electrical energy to the heart 501 under certain predetermined conditions to treat cardiac arrhythmias. The lead system 502 may include one or more electrodes used for pacing, sensing, and/or defibrillation.

In the embodiment shown in FIG. 5, the lead system 502 includes an intracardiac right ventricular (RV) lead system 504, an intracardiac right atrial (RA) lead system 505, an intracardiac left ventricular (LV) lead system 506, and an extracardiac left atrial (LA) lead system 508. The lead system 502 of FIG. 5 illustrates one embodiment that may be used in connection with the capture testing management methodologies described above. Other leads and/or electrodes may additionally or alternatively be used.

The lead system 502 may include intracardiac leads 504, 505, 506 implanted in a human body with portions of the intracardiac leads 504, 505, 506 inserted into a heart 501. The intracardiac leads 504, 505, 506 include various electrodes positionable within the heart for sensing electrical activity of the heart and for delivering electrical stimulation energy to the heart, for example, pacing pulses and/or defibrillation shocks to treat various arrhythmias of the heart.

As illustrated in FIG. 5, the lead system 502 may include one or more extracardiac leads 508 having electrodes, e.g., epicardial electrodes, positioned at locations outside the heart for sensing and pacing one or more heart chambers.

The right ventricular lead system 504 illustrated in FIG. 5 includes an SVC-coil 516, an RV-coil 514, an RV-ring electrode 511, and an RV-tip electrode 512. The right ventricular lead system 504 extends through the right atrium 520 and into the right ventricle 519. In particular, the RV-tip electrode 512, RV-ring electrode 511, and RV-coil electrode 514 are positioned at appropriate locations within the right ventricle 519 for sensing and delivering electrical stimulation pulses to the heart. The SVC-coil 516 is positioned at an appropriate location within the right atrium chamber 520 of the heart 501 or a major vein leading to the right atrial chamber 520 of the heart 501.

In one configuration, the RV-tip electrode 512 referenced to the can electrode 609 may be used to implement unipolar pacing and/or sensing in the right ventricle 519. Bipolar pacing and/or sensing in the right ventricle may be implemented using the RV-tip 512 and RV-ring 511 electrodes. In yet another configuration, the RV-ring 511 electrode may optionally be omitted, and bipolar pacing and/or sensing may be accomplished using the RV-tip electrode 512 and the RV-coil 514, for example. The right ventricular lead system 504 may be configured as an integrated bipolar pace/shock lead. The RV-coil 514 and the SVC-coil 516 are defibrillation electrodes.

The left ventricular lead 506 includes an LV distal electrode 513 and an LV proximal electrode 517 located at appropriate locations in or about the left ventricle 524 for pacing and/or sensing the left ventricle 524. The left ventricular lead 506 may be guided into the right atrium 520 of the heart via the superior vena cava. From the right atrium 520, the left ventricular lead 506 may be deployed into the coronary sinus ostium, the opening of the coronary sinus 550. The lead 506 may be guided through the coronary sinus 550 to a coronary vein of the left ventricle 524. This vein is used as an access pathway for leads to reach the surfaces of the left ventricle 524 which are not directly accessible from the right side of the heart. Lead placement for the left ventricular lead 506 may be achieved via subclavian vein access and a preformed guiding catheter for insertion of the LV electrodes 513, 517 adjacent to the left ventricle.

Unipolar pacing and/or sensing in the left ventricle may be implemented, for example, using the LV distal electrode referenced to the can electrode 609. The LV distal electrode 513 and the LV proximal electrode 517 may be used together as bipolar sense and/or pace electrodes for the left ventricle. The left ventricular lead 506 and the right ventricular lead 504, in conjunction with the ICD 500, may be used to provide cardiac resynchronization therapy such that the ventricles of the heart are paced substantially simultaneously, or in phased sequence, to provide enhanced cardiac pumping efficiency for patients suffering from chronic heart failure.

The right atrial lead 505 includes a RA-tip electrode 556 and an RA-ring electrode 554 positioned at appropriate locations in the right atrium 520 for sensing and pacing the right atrium 520. In one configuration, the RA-tip 556 referenced to the can electrode 609, for example, may be used to provide unipolar pacing and/or sensing in the right atrium 520. In another configuration, the RA-tip electrode 556 and the RA-ring electrode 554 may be used to effect bipolar pacing and/or sensing.

FIG. 5 illustrates one embodiment of a left atrial lead system 508. In this example, the left atrial lead 508 is implemented as an extracardiac lead with LA distal 518 and LA proximal 515 electrodes positioned at appropriate locations outside the heart 501 for sensing and pacing the left atrium 522. Unipolar pacing and/or sensing of the left atrium may be accomplished, for example, using the LA distal electrode 518 to the can 609 pacing vector. The LA proximal 515 and LA distal 518 electrodes may be used together to implement bipolar pacing and/or sensing of the left atrium 522.

Figure 6:
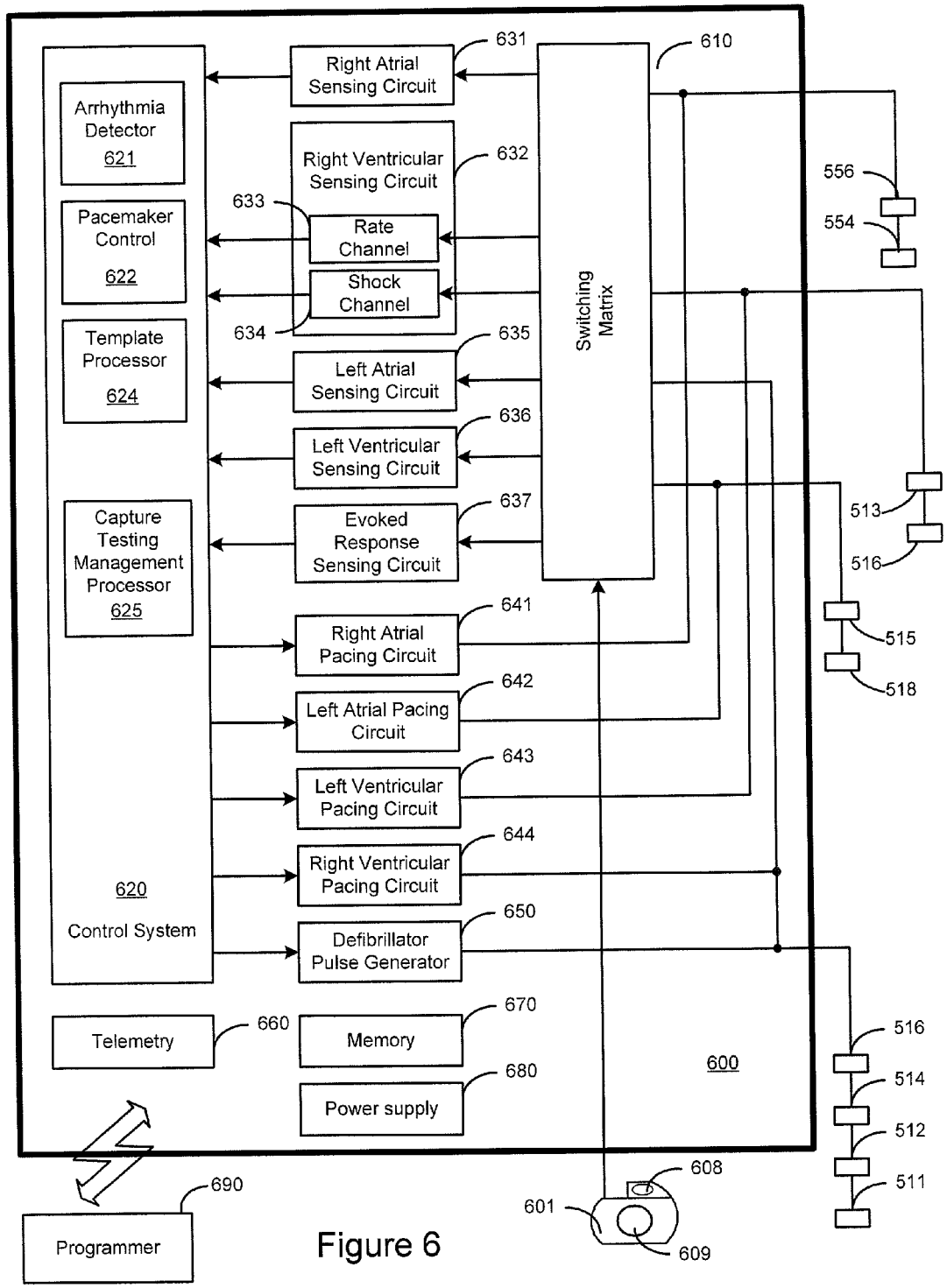
FIG. 6 is a block diagram of an implantable medical device that may be used to implement capture testing management methods in accordance with embodiments of the invention.

Referring now to FIG. 6, there is shown an embodiment of a cardiac defibrillator 600 suitable for implementing a capture testing management methods of the present invention. FIG. 6 shows a cardiac defibrillator divided into functional blocks. It is understood by those skilled in the art that there exist many possible configurations in which these functional blocks can be arranged. The example depicted in FIG. 6 is one possible functional arrangement. Other arrangements are also possible. For example, more, fewer or different functional blocks may be used to describe a cardiac defibrillator suitable for implementing the capture testing management methods of the present invention. In addition, although the cardiac defibrillator 600 depicted in FIG. 6 contemplates the use of a programmable microprocessor-based logic circuit, other circuit implementations may be utilized.

The cardiac defibrillator 600 depicted in FIG. 6 includes circuitry for receiving cardiac signals from a heart and delivering electrical stimulation energy to the heart in the form of pacing pulses or defibrillation shocks. In one embodiment, the circuitry of the cardiac defibrillator 600 is encased and hermetically sealed in a housing 601 suitable for implanting in a human body. Power to the cardiac defibrillator 600 is supplied by an electrochemical battery 680. A connector block (not shown) is attached to the housing 601 of the cardiac defibrillator 600 to allow for the physical and electrical attachment of the lead system conductors to the circuitry of the cardiac defibrillator 600.

The cardiac defibrillator 600 may be a programmable microprocessor-based system, including a control system 620 and a memory 670. The memory 670 may store parameters for various pacing, defibrillation, and sensing modes, along with other parameters. Further, the memory 670 may store data indicative of cardiac signals received by other components of the cardiac defibrillator 600. The memory 670 may be used, for example, for storing historical EGM and therapy data. The historical data storage may include, for example, data obtained from long term patient monitoring used for trending or other diagnostic purposes. Historical data, as well as other information, may be transmitted to an external programmer unit 690 as needed or desired.

The control system 620 and memory 670 may cooperate with other components of the cardiac defibrillator 600 to control the operations of the cardiac defibrillator 600. The control system depicted in FIG. 6 incorporates a capture testing management processor 625 for managing capture testing in response to comparisons of evoked response templates with post-shock evoked response signals in accordance with various embodiments of the present invention. The control system 620 may include additional functional components including a pacemaker control circuit 622, an arrhythmia detector 621, and a template processor 624, along with other components for controlling the operations of the cardiac defibrillator 600. For example, capture testing management processor 625 may determine myocardial stability and communicate to control system 620 to turn-on various CRM features based on the patient's cardiac condition.

Telemetry circuitry 660 may be implemented to provide communications between the cardiac defibrillator 600 and an external programmer unit 690. In one embodiment, the telemetry circuitry 660 and the programmer unit 690 communicate using a wire loop antenna and a radio frequency telemetric link, as is known in the art, to receive and transmit signals and data between the programmer unit 690 and the telemetry circuitry 660. In this manner, programming commands and other information may be transferred to the control system 620 of the cardiac defibrillator 600 from the programmer unit 690 during and after implant. In addition, stored cardiac data pertaining to evoked response thresholds, capture detection and/or capture testing, for example, along with other data, may be transferred to the programmer unit 690 from the cardiac defibrillator 600.

In addition, telemetry circuitry 660 may be implemented to provide communications between the cardiac defibrillator 600 and an advanced patient management (APM) system (not shown) in accordance with implementations of the present invention. Advanced patient management (APM) systems involve a system of medical devices that are accessible through various communications technologies. Medical information may be transmitted to a remote patient management server from the various medical devices. The medical information may be analyzed and used to diagnose and/or monitor disease progression, to determine and control delivery of appropriate therapies for the patient, and/or for other medical purposes. Advanced patient management techniques, aspects of which may be utilized in systems and methods providing capture testing management in accordance with embodiments of the invention, are further described in U.S. Pat. Nos. 6,336,903, 6,312,378, 6,270,457, and 6,398,728 which are incorporated herein by reference. For example APM systems can store patient history data and can use the historical data in combination with baseline and post-shock data to treat patient conditions or to alert a patient's physician of diminishing patient conditions. Alternatively, the defibrillator 600 may be offline from the APM for a period of time and then may be turned online when patient conditions dictate cooperation between the defibrillator 600 and APM system.

In the embodiment of the cardiac defibrillator 600 illustrated in FIG. 6, electrodes RA-tip 556, RA-ring 554, RV-tip 512, RV-ring 511, RV-coil, SVC-coil, LV distal electrode 513, LV proximal electrode 517, LA distal electrode 518, LA proximal electrode 515, indifferent electrode 608, and can electrode 609 are coupled through a switch matrix 610 to sensing circuits 631-637.

A right atrial sensing circuit 631 serves to detect and amplify electrical signals from the right atrium of the heart. Bipolar sensing in the right atrium may be implemented, for example, by sensing voltages developed between the RA-tip 556 and the RA-ring 554. Unipolar sensing may be implemented, for example, by sensing voltages developed between the RA-tip 556 and the can electrode 609. Outputs from the right atrial sensing circuit are coupled to the control system 620.

A right ventricular sensing circuit 632 serves to detect and amplify electrical signals from the right ventricle of the heart. The right ventricular sensing circuit 632 may include, for example, a right ventricular rate channel 633 and a right ventricular shock channel 634. Right ventricular cardiac signals sensed through use of the RV-tip 512 electrode are right ventricular near-field signals and are denoted RV rate channel signals. A bipolar RV rate channel signal may be sensed as a voltage developed between the RV-tip 512 and the RV-ring. Alternatively, bipolar sensing in the right ventricle may be implemented using the RV-tip electrode 512 and the RV-coil 514. Unipolar rate channel sensing in the right ventricle may be implemented, for example, by sensing voltages developed between the RV-tip 512 and the can electrode 609.

Right ventricular cardiac signals sensed through use of the RV-coil electrode 514 are far-field signals, also referred to as RV morphology or RV shock channel signals. More particularly, a right ventricular shock channel signal may be detected as a voltage developed between the RV-coil 514 and the SVC-coil 516. A right ventricular shock channel signal may also be detected as a voltage developed between the RV-coil 514 and the can electrode 609. In another configuration the can electrode 609 and the SVC-coil electrode 516 may be electrically shorted and a RV shock channel signal may be detected as the voltage developed between the RV-coil 514 and the can electrode 609/SVC-coil 516 combination.

Outputs from the right ventricular sensing circuit 632 are coupled to the control system 620. In one embodiment of the invention, rate channel signals and shock channel signals may be used to develop templates for analyzing cardiac signals. In this embodiment, rate channel signals and shock channel signals may be transferred from the right ventricular sensing circuit 632 to the control system 620 and to a template processor 624 where the characteristics, such as morphological characteristics, of a cardiac signal are analyzed. The template processor 624 works in combination with the control system 620 and the memory 670 to generate and maintain various types of templates, including, for example, templates used for arrhythmia discrimination as well as baseline evoked response templates used in accordance with embodiments of the invention.

The stored templates may be updated periodically. A template update procedure may be initiated, for example, automatically or by an external template update command. A template update command may be made by a physician and communicated to the cardiac defibrillator 600 through the external programmer 690, for example. An automatic template update procedure may involve periodically updating one or more templates without external initiation. For example, one or more templates may be updated daily, weekly, or according to another time basis. The template processor 624 may determine an optimal time for attempting a template update, e.g., during the patient's normal sleep time.

Left atrial cardiac signals may be sensed through the use of one or more left atrial electrodes 515, 518, which may be configured as epicardial electrodes. A left atrial sensing circuit 635 serves to detect and amplify electrical signals from the left atrium of the heart. Bipolar sensing and/or pacing in the left atrium may be implemented, for example, using the LA distal electrode 518 and the LA proximal electrode 515. Unipolar sensing and/or pacing of the left atrium may be accomplished, for example, using the LA distal electrode 518 to can vector 609 or the LA proximal electrode 515 to can vector 609.

A left ventricular sensing circuit 636 serves to detect and amplify electrical signals from the left ventricle of the heart. Bipolar sensing in the left ventricle may be implemented, for example, by sensing voltages developed between the LV distal electrode 513 and the LV proximal electrode 517. Unipolar sensing may be implemented, for example, by sensing voltages developed between the LV distal electrode 513 or the LV proximal electrode 517 to the can electrode 609.

Optionally, an LV coil electrode (not shown) may be inserted into the patient's cardiac vasculature, e.g., the coronary sinus, adjacent the left heart. Signals detected using combinations of the LV electrodes, 513, 517, LV coil electrode (not shown), and/or can electrodes 609 may be sensed and amplified by the left ventricular sensing circuitry 636. The output of the left ventricular sensing circuit 636 is coupled to the control system 620.

The outputs of the switching matrix 610 may be operated to couple selected combinations of electrodes 511, 512, 513, 514, 515, 516, 517, 518, 556, 554 to an evoked response sensing circuit 637. The evoked response sensing circuit 637 serves to sense and amplify voltages developed using various combinations of electrodes for management of capture testing in accordance with embodiments of the invention.

In the embodiments described below, various combinations of pacing and sensing electrodes may be utilized in connection with pacing and sensing the cardiac signal following the pace pulse to sense an evoked response. For example, in some embodiments, a first electrode combination is used for pacing a heart chamber and a second electrode combination is used to sense the evoked response following pacing. In other embodiments, the same electrode combination is used for pacing and sensing.

The pacemaker control circuit 622, in combination with pacing circuitry for the left atrium, right atrium, left ventricle, and right ventricle 641, 642, 643, 644, may be implemented to selectively generate and deliver pacing pulses to the heart using various electrode combinations. The pacing electrode combinations may be used to effect bipolar or unipolar pacing of the heart chambers as described above.

As described above, bipolar or unipolar pacing pulses may be delivered to a heart chamber using one of the pacing vectors as described above. The electrical signal following the delivery of the pacing pulses may be sensed through various sensing vectors coupled through the switch matrix 610 to the evoked response sensing circuit 637 and used for the management of capture testing.

Possible sensing vectors for effecting capture testing management may include, for example, RV-tip 512 and RV-coil 514, RV-coil 514 and LV distal electrode 513, RV coil 514 and LV proximal electrode 517, RV-coil 514 and can 609, RV-coil 514 and SVC coil 516, RV-coil 514 and SVC coil 516 tied and the can 609, RV-coil 514 and A-ring 554, RV-coil 514 and RA-tip 556, LV distal electrode 513 and LV proximal electrode 517, LV distal electrode 513 and can 609, LV distal electrode 513 and SVC coil 516, LV distal electrode 513 and A-ring 554, LV distal electrode 513 and A-tip 556, LV proximal electrode 517 and can 609, LV proximal electrode 517 and SVC coil 516, LV proximal electrode 517 and A-ring 554, LV proximal electrode 517 and RA-tip 556, SVC coil 516 and can 609, RA-ring 554 and can 609, RA-tip 556 and can 609, SVC coil 516 and A-ring 554, SVC coil 516 and RA-tip 556 and RA-ring 554 and RA-tip 556. This list is not exhaustive and other sensing vector combinations may be developed to implement capture testing management in accordance with embodiments of the invention. For example, other combinations may include a coronary sinus electrode, an indifferent electrode, a leadless ECG electrode, cardiac epicardial electrodes, subcutaneous electrodes, and/or other electrodes.

Approaches for using leadless ECG electrodes for capture detection are described in U.S. Pat. No. 5,222,493, which is incorporated by reference in its entirety.

Subcutaneous electrodes may provide additional sensing vectors useable for capture testing management. In one implementation, cardiac rhythm management system may involve a hybrid system including a first device, e.g. a pacemaker coupled to an intracardiac lead system, configured to pace the heart, and a second device, e.g. a defibrillator coupled to a subcutaneous lead system, configured to perform functions other than pacing. The second device may be employed to manage capture testing based on signals sensed using subcutaneous electrode arrays. The first and second devices may operate cooperatively with communication between the devices occurring over a wireless link, for example. Examples of subcutaneous electrode systems and devices are described in commonly owned U.S. patent application Ser. Nos. 10/462,001, filed Jun. 13, 2003, now U.S. Publication No. 2004/0230229 and 10/465,520, filed Jun. 19, 2003, now U.S. Publication No. 2004/0230230, which are incorporated herein by reference in their respective entireties.

For right ventricular pacing, bipolar pacing may be delivered using the RV-tip electrode 512 and the RV-ring electrode 511. Unipolar pacing may be delivered using the RV-tip 512 to can 609 vector. A useful sensing electrode combinations for cardiac response classification following RV pacing include RV-coil 514 to SVC-coil 516 tied to the can electrode 609, RV-coil 514 to can electrode 609, and, if the system includes an left ventricular lead, LV distal electrode 513 to LV proximal electrode 517.

In an example of left ventricular pacing, bipolar pacing pulses may be delivered to the left ventricle between the LV distal electrode 513 and the LV proximal electrode 517. In another example, unipolar pacing pulses may be delivered to the left ventricle, for example, between the LV distal electrode 513 and the can 609. The cardiac signal following the delivery of the pacing pulses may preferably be sensed using the LV proximal electrode 517 and the can 609.

In an example of right atrial pacing, bipolar pacing pulses may be delivered to the right atrium between the RA-tip electrode 556 and the RA-ring electrode 554. In another example, unipolar pacing pulses may be delivered to the right atrium, for example, between the RA-tip electrode 556 and the can electrode 609. For unipolar right atrial pacing, a useful electrode combination for sensing cardiac signals following pacing for cardiac response classification comprises the RA-ring 554 to indifferent electrode.

In an example of left atrial pacing, bipolar pacing pulses may be delivered to the left atrium between the LA distal electrode 518 and the LA proximal electrode 515. In another example, unipolar pacing pulses may be delivered to the left atrium, for example, between the LA distal electrode 518 and the can electrode 609. The cardiac signal following the delivery of the pacing pulses and used for cardiac response classification may be sensed using the RA-tip 556 to RA-ring 554 vector.

In one embodiment of the invention, a switching matrix 610 is coupled to the RA-tip 556, RA-ring 554, RV-tip 512, RV-coil 514, LV distal electrode 513, LV proximal electrode 517, SVC coil 516, LA distal electrode 518, LA proximal electrode 515, indifferent, and can 609 electrodes. The switching matrix 610 may be arranged to provide connections to various configurations of pacing and defibrillation electrodes. The outputs of the switching matrix 610 are coupled to an evoked response (ER) sensing circuit 637 that serves to sense and amplify cardiac signals detected between the selected combinations of electrodes. The detected signals are coupled through the ER amplifier 637 to a capture testing management processor 625. The capture testing management processor 625 includes circuitry configured to acquire and compare evoked response templates with post-shock evoked response signals.

Various modifications and additions can be made to the preferred embodiments discussed hereinabove without departing from the scope of the present invention. Accordingly, the scope of the present invention should not be limited by the particular embodiments described above, but should be defined only by the claims set forth below and equivalents thereof.

What is claimed is:

1. An implantable system, comprising:
electrodes configured to electrically couple to a heart;
a pulse generator coupled to the electrodes, the pulse generator configured to deliver electrical therapy for the heart;
a sensing system coupled to the electrodes and configured to sense a cardiac signal associated with delivery of electrical therapy to the heart using the electrodes; and
circuitry configured to manage capture testing, the circuitry configured to acquire a post-therapy evoked response signal subsequent to delivery of a high energy therapy using signals received from the sensing system, compare a baseline evoked response template and the post-therapy evoked response signal, determine whether the high energy therapy rendered myocardial tissue of the heart unstable based on the comparison, and determine whether to enable, disable or adjust capture testing based at least in part on whether the high energy therapy rendered myocardial tissue of the heart unstable.

2. The system of claim 1, wherein the capture testing comprises automatic capture verification testing, the circuitry configured to disable or adjust automatic capture verification testing in response to the comparison indicating that the high energy therapy rendered myocardial tissue of the heart unstable.

3. The system of claim 1, wherein the high energy therapy comprises an anti-tachycardia pacing therapy.

4. The system of claim 1, wherein the high energy therapy comprises a cardioversion or a defibrillation therapy.

5. The system of claim 1, wherein the circuitry is configured to enable capture testing in response to assessing stability of the myocardial tissue based on the comparison indicating similarity between the baseline evoked response template and the post-therapy evoked response signal before expiration of a predetermined duration.

6. The system of claim 1, wherein the circuitry is configured to continue disablement of capture testing in response to continued instability of the myocardial tissue based on continued dissimilarity between the baseline evoked response template and multiple post-therapy evoked response signals obtained over at least a predetermined duration.

7. The system of claim 1, comprising communications circuitry coupled to the circuitry, wherein the circuitry and the communications circuitry cooperate to generate and transmit a message indicating continued instability of the myocardial tissue.

8. An implantable system, comprising:
electrodes configured to electrically couple to a heart;
a pulse generator coupled to the electrodes, the pulse generator configured to deliver electrical therapy for the heart;
a sensing system coupled to the electrodes and configured to sense a cardiac signal associated with delivery of electrical therapy to the heart using the electrodes; and
circuitry configured to manage one or more features of the implantable system, the circuitry configured to acquire a post-therapy evoked response signal subsequent to delivery of a high energy therapy using signals received from the sensing system, compare a baseline evoked response template and the post-therapy evoked response signal, determine whether the high energy therapy one or both of stunned and permanently changed myocardial tissue of the heart based on the comparison, disable the one or more features for a period of time that is longer than multiple cardiac cycles if the comparison indicates that the high energy therapy stunned the myocardial tissue, and adjust the one or more features if the comparison indicates that the high energy therapy permanently changed the myocardial tissue.

9. The system of claim 8, wherein the circuitry is configured to enable, disable or adjust each of a therapy feature, a monitoring feature, and a diagnostic feature based on the comparison.

10. The system of claim 8, wherein the one or more features comprises an automatic capture verification testing feature.

11. The system of claim 8, wherein the circuitry is configured to disable an automatic capture verification testing feature for a predetermined period of time based on the comparison indicating myocardial tissue instability.

12. An implantable system, comprising:
electrodes configured to electrically couple to a heart;
a pulse generator coupled to the one or more electrodes, the pulse generator configured to deliver electrical therapy to the heart;
a sensing system coupled to the one or more electrodes and configured to sense a cardiac signal associated with delivery of electrical therapy to the heart using the electrodes; and
circuitry configured to manage capture testing, the circuitry configured to acquire a post-therapy evoked response signal subsequent to high energy therapy delivery using signals received from the sensing system, compare a baseline evoked response template and the post-therapy evoked response signal, and determine whether to enable, disable or adjust capture testing based on the comparison indicating that the high energy therapy rendered myocardial tissue of the heart unstable.

13. The system of claim 12, wherein the circuitry is configured to perform automatic capture verification testing.

14. The system of claim 12, wherein the circuitry is configured to perform autothreshold testing.

15. The system of claim 12, wherein the circuitry is configured to compare the morphologies of the baseline template and the post-therapy evoked response signal.

16. The system of claim 12, wherein the circuitry is configured to assess stability of the myocardial tissue subsequent to high energy therapy delivery based at least in part on a predetermined period of time the myocardial tissue takes to return to a pre-therapy state.

17. The system of claim 12, wherein the circuitry is configured to enable capture testing in response to the comparison indicating stability of the myocardial tissue within a predetermined duration.

18. The system of claim 12, wherein the circuitry is configured to continue disablement of capture testing in response to continued instability of the myocardial tissue for at least a predetermined duration.

19. The system of claim 12, comprising communications circuitry, wherein the circuitry and communications circuitry cooperate to generate and transmit a message indicating continued instability of the myocardial tissue.

20. The system of claim 12, wherein the circuitry is configured to acquire a new baseline template using the received signals upon continued instability of the myocardial tissue.

* * * * *